US012667630B2

(12) United States Patent
Kung et al.

(10) Patent No.: US 12,667,630 B2
(45) Date of Patent: Jun. 30, 2026

(54) RADIOACTIVELY LABELED LIGAND FOR FIBROBLAST ACTIVATION PROTEIN-ALPHA IMAGING AGENT AND PREPARATION METHOD THEREFOR

(71) Applicants: FIVE ELEVEN PHARMA, INC, Philadelphia, PA (US); BIOMOLECULAR PROBES BIOTECHNOLOGY (BEIJING) CO., LTD, Beijing (CN)

(72) Inventors: Hank F Kung, Philadelphia, PA (US); Zhihao Zha, Beijing (CN); Karl Ploessl, Philadelphia, PA (US); Seok Rye Choi, Philadelphia, PA (US); David Alexoff, Philadelphia, PA (US)

(73) Assignees: FIVE ELEVEN PHARMA, INC, Philadelphia, PA (US); BIOMOLECULAR PROBES BIOTECHNOLOGY (BEIJING) CO., LTD, Beijing (CN)

( * ) Notice: Subject to any disclaimer, the term of this patent is extended or adjusted under 35 U.S.C. 154(b) by 554 days.

(21) Appl. No.: 18/263,722

(22) PCT Filed: Feb. 1, 2021

(86) PCT No.: PCT/CN2021/074671
§ 371 (c)(1),
(2) Date: Aug. 1, 2023

(87) PCT Pub. No.: WO2022/160338
PCT Pub. Date: Aug. 4, 2022

(65) Prior Publication Data

US 2024/0139350 A1 May 2, 2024

(51) Int. Cl.
*A61K 51/04* (2006.01)

(52) U.S. Cl.
CPC ...... *A61K 51/0455* (2013.01); *A61K 2123/00* (2013.01)

(58) Field of Classification Search
CPC ............................ A61K 51/04; A61K 2123/00
See application file for complete search history.

(56) References Cited

U.S. PATENT DOCUMENTS

2014/0357650 A1* 12/2014 Jansen ................. C07D 413/12 548/200

FOREIGN PATENT DOCUMENTS

| | | | |
|---|---|---|---|
| CN | 111699181 | A | 9/2020 |
| CN | 111991570 | A | 11/2020 |
| CN | 112194651 | A | 1/2021 |
| WO | 2021005125 | A1 | 1/2021 |

OTHER PUBLICATIONS

Eder, Matthias et al.; "68Ga-Complex Lipophilicity and the Targeting Property of a Urea-Based PSMA Inhibitor for PET Imaging", Bioconjugate Chemistry, vol. 23, Feb. 28, 2012; pp. 688-697.
Liolios, Christos et al.; "Synthesis characterization and evaluation of 68Ga labelled monomeric and dimeric quinazoline derivatives of the HBED-CC chelator targeting the epidermal growth factor receptor", Bioorganic Chemistry, vol. 100, 103855; Apr. 26, 2020; pp. 1-9.
Liolios, Christos et al.; "Monomeric and Dimeric 68Ga-Labeled Bombesin Analogues for Positron Emission Tomography (PET) Imaging of Tumors Expressing Gastrin-Releasing Peptide Receptors (GRPrs)", Journal of Medicinal Chemistry, vol. 61, Feb. 12, 2018; pp. 2062-2074.
Giesel, Frederik L. et al.; "68Ga-FAPI PET/CT: Biodistribution and Preliminary Dosimetry Estimate of 2 DOTA-Containing FAP-Targeting Agents in Patients with Various Cancers", The Journal of Nuclear Medicine, vol. 60, No. 3, Mar. 31, 2019; pp. 386-392.

* cited by examiner

*Primary Examiner* — Michael G. Hartley
*Assistant Examiner* — Jagadishwar R Samala
(74) *Attorney, Agent, or Firm* — NKL Law; Allen Xue

(57) ABSTRACT

A radioactively labeled ligand for a fibroblast activation protein-alpha imaging agent and a preparation method therefor are provided. The radioactively labeled ligand for the fibroblast activation protein-alpha imaging agent has structural formal (I). The compound has a good $^{68}$Ga labeling property, a high stability and a good affinity for FAP tumors. The radioactively labeled ligand for $^{68}$Ga-labeled FAPi can be used as a tumor positron imaging agent.

7 Claims, 1 Drawing Sheet

RADIOACTIVELY LABELED LIGAND FOR FIBROBLAST ACTIVATION PROTEIN-ALPHA IMAGING AGENT AND PREPARATION METHOD THEREFOR

TECHNICAL FIELD OF THE INVENTION

This present invention relates to a novel radionuclide-labeled ligand (precursor) and a preparation method therefor, and particularly, to a radioactively labeled ligand for $^{68}$Ga-labeled fibroblast activation protein-alpha (FAP) targeted imaging agent and a preparation method therefor, and belongs to the field of radiolabeled compounds.

BACKGROUND

Fibroblast activation protein-alpha (FAP) is a cell surface serine protease, which acts on multiple hormones and extracellular matrix components. FAP has high levels of expression in a variety of cancers and is often used as a biomarker of pro-tumorigenic mechanisms. In recent years, FAP has been used as a molecular target for cancer diagnostic therapy, and a large number of FAP-targeted therapies have entered the design and testing phase.

Fibroblast activation protein-alpha (FAP) is discovered independently in the mid-1980s and the early 1990s by two research groups with different topics. Retting et al. first described and named FAP based on its expression on fibroblasts when studying surface antigens in 1986. The other group was Aoyama et al., who found a Gelatinase expressed on the surface of invasive Melanoma cells when studying the protease on membrane surface, and named it "seprase". Until 1997, gene sequencing results demonstrated that FAP and seprase were the same protein molecule. FAP, like other DPP enzymes, belongs to the dipeptidyl peptidase (DPP) family and has post-proline exopeptidase activity. However, FAP has unique gelatinase activity, and it can be denatured for degradation or cleaved by matrix metalloproteinases (MMP). Structurally, FAP consists of a 6 amino acid cytoplasmic tail, a transmembrane domain of 20 amino acids, and an extracellular domain of 734 amino acids, the exodomain consists of an eight-bladed β-propeller, and α/β-hydrolase domain serving as substrate selectivity gate. The FAP monomer is inactive but forms active homodimers and heterodimers with dipeptidyl peptidase IV (DPPIV) of the closest family member. Different from DPPIV, FAP is only expressed in the fibroblasts of fetal cells, stromal fibroblasts, wounded tissues, and more than 90% of malignant tumors, but not in benign tumors or normal adult tissues. In normal adult tissues, FAP is only expressed in bone marrow mesenchymal stem cells (BM-MSC). Whereas in tumors, FAP is expressed in various mesenchymal cells, including mesenchymal stem cells (MSCs), cancer-associated fibroblasts (CAFs), sarcomas, and melanoma cells. CAFs, also known as tumor-associated fibroblasts and activated fibroblasts, are a cell type in the tumor microenvironment and play an auxiliary role in tumor growth and invasion. They promote the remodeling of the extracellular matrix, enhance the invasiveness and angiogenesis ability of tumors, and can induce epithelial-mesenchymal transformation by secreting growth factors and cytokines. In addition, CAFs are also involved in immune interactions between tumor and host. Many studies have made FAP a marker for CAFs based on their high expression in CAFs.

FAP-targeted imaging has a great advantage in tumor PET imaging, as supportive matrices formed while tumor lesions are over 1-2 mm. The volume of stromal cells is larger than that of cancer cells. Thus, if FAP expresses sufficiently, matrix-targeted PET imaging will be more sensitive than glucose metabolism PET imaging. FAP-targeted PET imaging also has great advantages in detecting tumors with low or heterogeneous glucose metabolism or tumors near normal tissue with high Glycolysis. Other potential advantages include early imaging within 10 minutes after injection and no fasting, etc. Lastly, this PET imaging can serve as an accurate predictive biomarker of response to treatment against any FAP in most cancers. However, due to its expression in many tissue remodeling processes, FAP is not cancer-specific. For example, this PET imaging may make it difficult to distinguish between chronic pancreatitis and pancreatic ductal adenocarcinoma. Conversely, FAP-targeted PET imaging might be helpful in many non-oncological imaging to diagnose myocardial infarction, chronic inflammatory diseases, pulmonary fibrosis, hepatic fibrosis, or kidney fibrosis.

Based on existing FAP inhibitors (FAPI), Thomas Lindner et al. reported a FAP-targeted radioactive molecular probe in 2018. A series of quinoline-based derivatives were synthesized, and $^{177}$Lu labeled thereto. The binding and internalization rates of the compounds were determined by using HT-1080 cells transfected with human or mouse FAP genes and human embryonic kidney cells transfected with CD26. All tracers showed over 90% internalization. To confirm target specificity, binding assays were also performed on human embryonic kidney cells expressing mouse FAP and dipeptidyl peptidase 4 (CD26), which has a high homology to human FAP. In these experiments, FAPI-02 and FAPI-04 showed strong binding to murine FAP, FAPI-04 had higher values and did not bind to CD26.

A small animal PET study was performed on FAPI compounds with better cell results in (HT-1080) FAP xenograft mice. $^{68}$Ga-FAPI-02 and $^{68}$Ga-FAPI-04 showed the highest tumor uptake at 1 h post-injection (SUV max of 0.88 and 1.2, respectively), and no significant decrease within 2 hours (SUV of 0.71 and 1.1, respectively). The targeting of $^{68}$Ga-FAPI-04 was also successfully demonstrated in the second xenograft model SK-LMS-1. In addition, target specificity was elucidated by blocking experiments on HT-1080 FAP xenografts.

In clinical application of breast cancer patients, diagnostic PET/CT scans were performed after 10 minutes, 1 hour, and 3 hours of intravenous injection of $^{68}$Ga-FAPI-04 on 2 patients with metastatic breast cancer. The results exhibited that the accumulation of tracer in metastases was high (SUV max of 7-15.5 and 15.3-29.9, respectively), and tracer uptake in normal tissues was very low.

Among all tested derivatives, FAPI-04 is the most suitable theranostic tracer. Similar to its precursor FAPI-02, FAPI-04 could be internalized as a FAP-positive tumor and cleared from the body rapidly, resulting in very rapid accumulation at the tumor site (10 minutes after tracer administration) and a high tumor-to-organ ratio. In addition, the effective tumor uptake of FAPI-04 after 24 hours was 100% higher than FAPI-02, which has a great advantage in the oncology application of the tracer.

Based on the structure of FAPI-04, Anastasia Loktev et al. reported a series of novel FAP-targeted radioactive molecular probes in 2019, further improving the retention time of the drugs in tumors. The results of in vitro competition binding experiments showed that all compounds exhibited high binding to FAP, with values equal to or higher than those of FAPI-04 after incubation for 1 and 4 hours. Except for FAPI-38, the internalization rates of all compounds are equivalent to FAPI-04. Although most derivatives showed higher binding values than FAPI-04 after 24 hours, the clearance rate of compounds FAPI-38, -39, -40, and -41 from FAP-expressing cells was significantly accelerated.

FAP has received great attention as a radiodiagnostic and therapeutic target of emerging tumors, with high targeting, low background interference, and broad applicability to different tumors therefor. Although there are still many challenges, FAP has become the focus of the next nuclear medicine.

3,3'-(((2,2,13,13-tetramethyl-4,11-dioxo-3,12-dioxa-6,9-diaztetradecane-6,9-diyl) bis (methylene)) bis (4-hydroxy-3,1-phenylene) dipropionic acid (HBED) belongs to the non-macrocyclic class of bifunctional linkers and was not used in $^{68}Ga$ positron drug studies in early development. It was initially used as a soil fertilizer in coordination with $Fe^{3+}$ to cure iron deficiency discoloration in plants. In recent years, research has found that HBED is an excellent $Ga^{3+}$ bifunctional linker, with much higher thermodynamically stable constants than other commonly used linkers (log $K_{ML}$: HBED: 38.5; DOTA: 21.3; NOTA: 31.0; AAZTA: 22.18). The energy required for HBED to coordinate to $Ga^{3+}$ is lower than other bifunctional linkers, therefore, the temperature required for $^{68}Ga$-HBED labeling is lower and the time is shorter. In the development of positron drugs, not only acted as a bifunctional linker, but HBED also provides additional targeting groups for the drug, increasing the affinity between positron drugs and the targets. When Eder M et al. developed prostate cancer positron drugs, they found that drugs containing HBED imaging had better uptake values for tumor cells compared to DOTA, and PET imaging of tumor mice indicated better tumor uptake as well as target/non-target ratio for HBED.

Thus, when combining HBED and FAP inhibitors as radiopharmaceuticals, it is possible to make the $^{68}Ga$ labeling reaction conditions much milder and more efficient, with better properties, and is expected to meet the needs of future diagnosis of clinical tumors. In addition, HBED-CC can also coordinate labeled F-18 with $[^{18}F]AlF$ for PET imaging and labeled with carbonyl technetium $^{99m}Tc(CO)_3$ and carbonyl rhenium $^{188/186}Re(CO)_3$ for radioactive formulations for SPECT imaging and treatment.

SUMMARY OF THE INVENTION

The present invention provides a radioactively labeled ligand for $^{68}Ga$-labeled fibroblast activation protein-alpha (FAP) imaging agent, which is convenient and efficient in preparation and has good in vivo biometabolic properties. It is a good tumor imaging pharmaceutical.

The present invention provides a preparation method for the aforementioned radioactively labeled ligand for $^{68}Ga$-labeled fibroblast activation protein-alpha (FAP) imaging agent.

The present invention provides the use of the aforementioned radioactively labeled ligand for $^{68}Ga$-labeled fibroblast activation protein-alpha (FAP) imaging agent as a tumor imaging agent.

One aspect of the present invention encompasses the aforementioned radioactively labeled ligand for fibroblast activation protein-alpha (FAP) imaging agent with the structural formula of

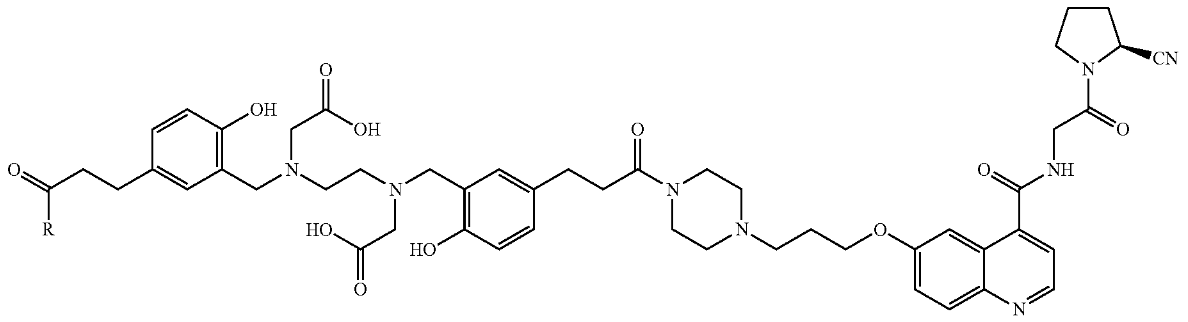

Wherein R is —OH or

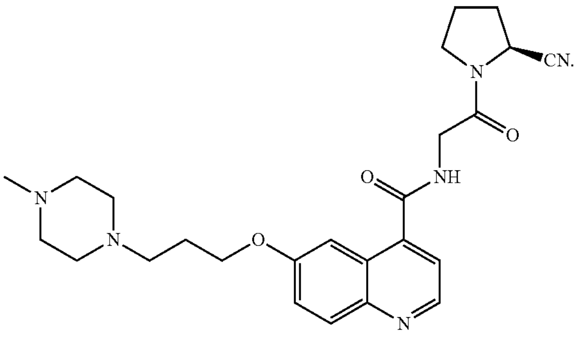 [SMILES: CN1CCN(CCCOc2ccc3nccc(C(=O)NCC(=O)N4CCC[C@H]4C#N)c3c2)CC1]

Another aspect of the present invention encompasses a preparation method of the aforementioned radioactively labeled ligand for fibroblast activation protein-alpha (FAP) imaging agent, with the steps performed as follows: the bifunctional linker HBED-CC and the FAP inhibitor are subjected to a condensation reaction in the presence of a base and a condensing agent, followed by deprotection of the protecting group with an acid to give the fibroblast activation protein (FAP) targeted imaging agent, which has the reaction formula as below:

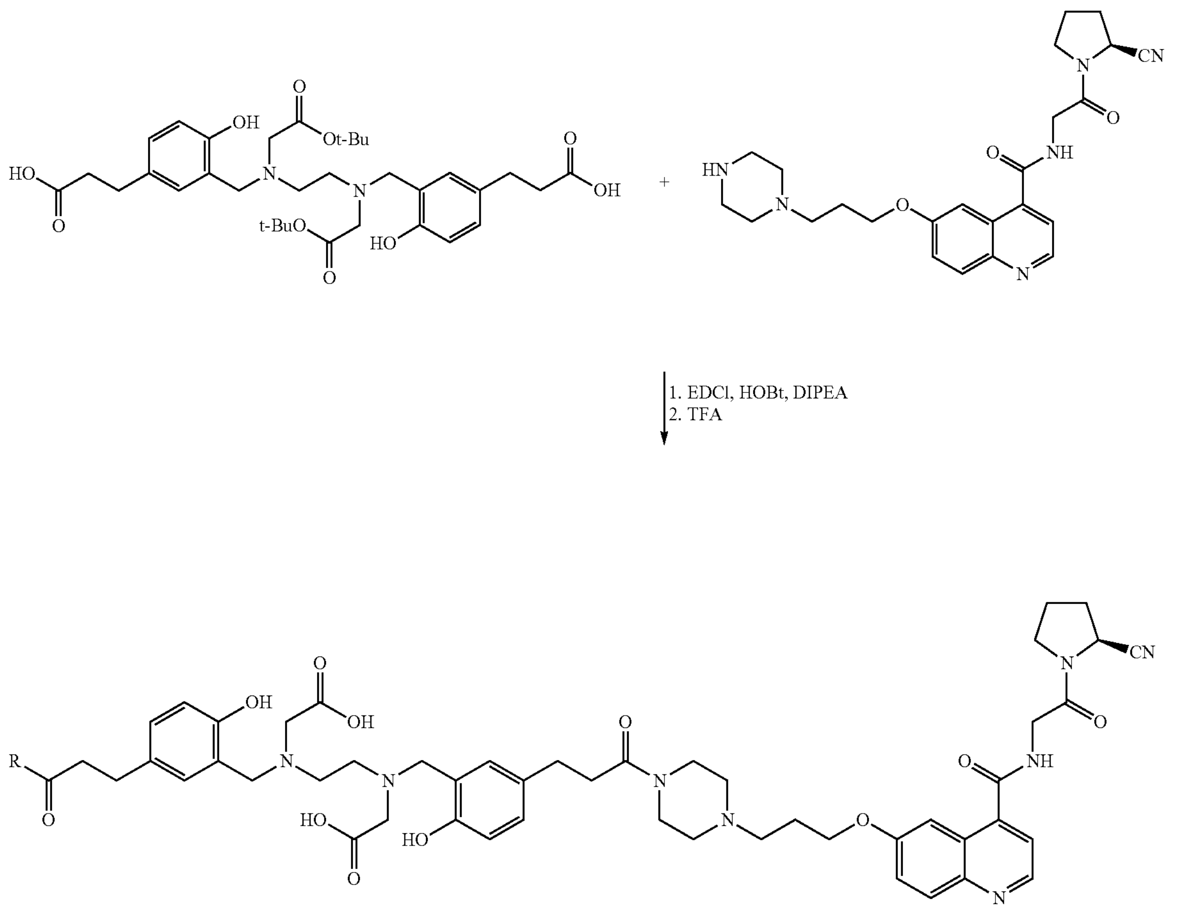

Wherein R is —OH or

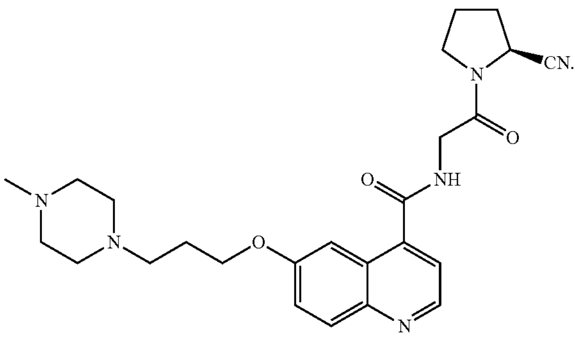 [SMILES: CN1CCN(CCCOc2ccc3nccc(C(=O)NCC(=O)N4CCC[C@H]4C#N)c3c2)CC1]

Yet another aspect of the present invention encompasses the use of the aforementioned radioactively labeled ligand for fibroblast activation protein-alpha (FAP) imaging agents in $^{68}Ga$ positron drugs. The chemical structure of this imaging agent comprises the bifunctional linker HBED, which binds to $^{68}Ga$ easily, thus making the radioactive preparation more convenient and efficient.

Benefits

The aforementioned radioactively labeled ligand for fibroblast activation protein-alpha (FAP) imaging agent, using the biological characteristic of specific targeting FAP therein, has important clinical potential values in early diagnosis, preoperative staging, treatment guidance, recurrence, and metastasis focus detection of tumors. It is expected to develop imaging agents with good biological properties.

The subject matter of the present invention is further illustrated and described in connection with the example and the corresponding text and figures. There is no intent to limit the protection scope of the present invention.

DETAILED DESCRIPTION

Figure 1:
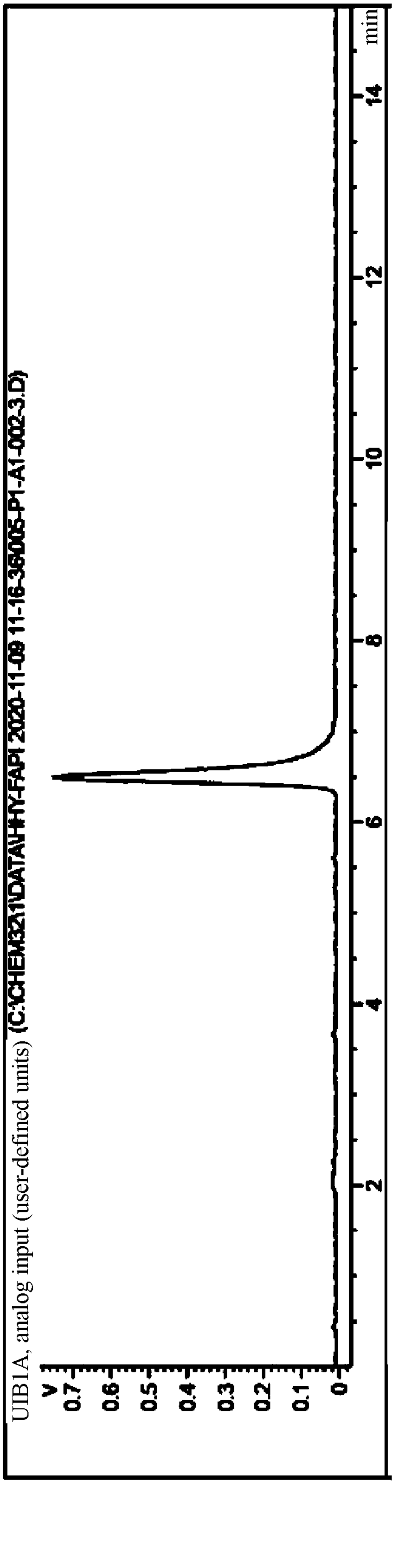
FIG. 1. HPLC chromatogram of $^{68}$GaA1-labeled reaction solution prepared in step-3 of Example 3 of the present invention.

Unless otherwise specified, the raw material and reagents mentioned in the examples of the present disclosure are the conventional ones that are commercially available, the test methods used are conventional, and the equipment and devices used are all conventional ones in this field.

Example 1

Synthesis of radioactively labeled ligand A1 for fibroblast activation protein-alpha (FAP) imaging agent.

(S)-3-(3-((carboxymethyl)(2-((carboxymethyl)(5-(3-(4-((4-((2-(2-cyanopyrrolidin-1-yl)-2-oxoethyl)carbamoyl)quinolin-6-yl)oxy)propyl)piperazin-1-yl)-3-oxopropyl)-2-hydroxybenzyl)amino)ethyl)amino)methyl)-4-hydroxyphenyl)propanoic Acid Synthesis reaction equation:

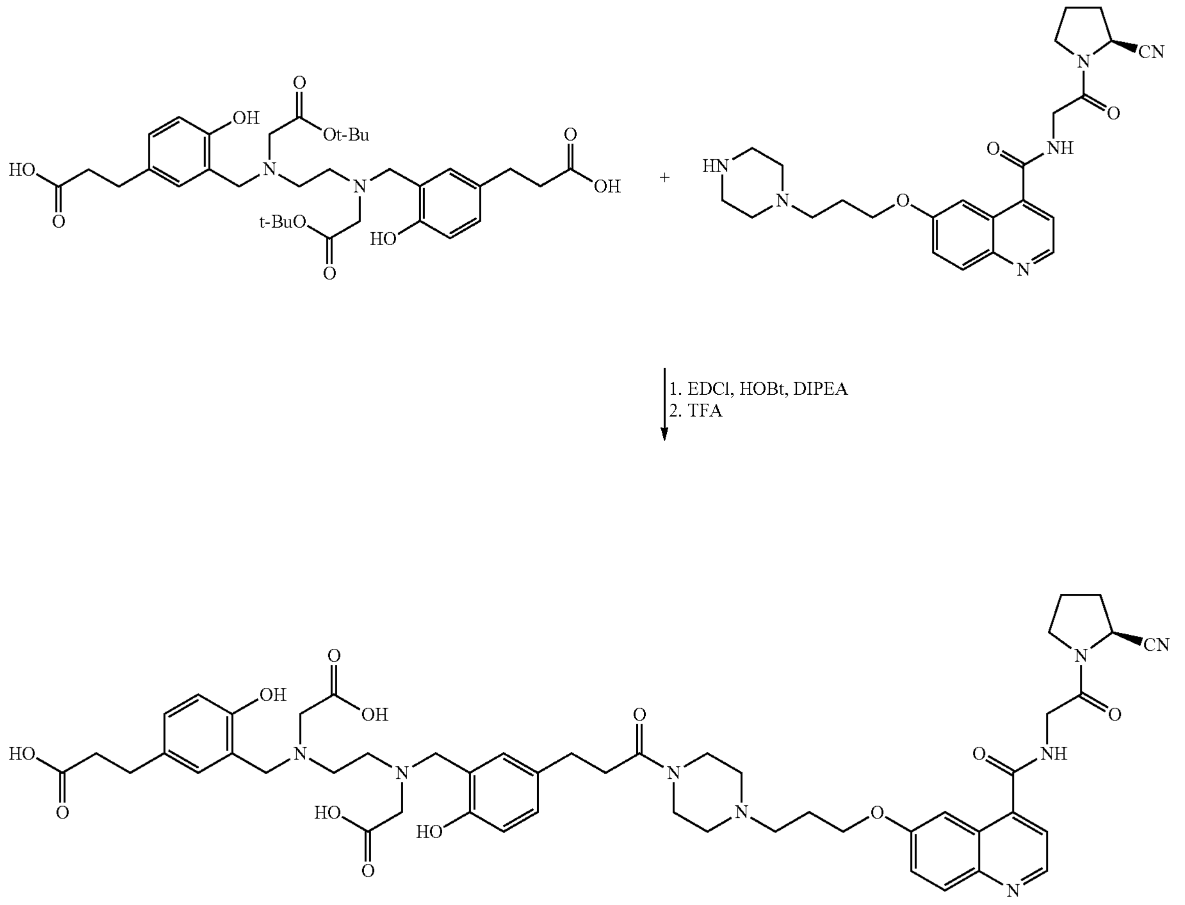

A1

Synthetic Methods

Compound 3,3'-(((2,2,13,13-tetramethyl-4,11-dioxo-3,12-dioxa-6,9-diazatetradecane-6,9-diyl) bis (methylene)) bis (4-hydroxy-3,1-phenylene) dipropanoic acid (64 mg, 0.1 mmol) was dissolved in 2 mL of dry dimethylformamide, 1-(3-dimethylaminopropyl)-3-ethylcarbodiimide (EDCI, 28.5 mg, 0.15 mmol), 1-hydroxybenzotriazole (HOBt, 25.3 mg, 0.15 mmol), N,N-diisopropylethylamine (DIPEA, 41.3 mg, 0.32 mmol) and (S)—N-(2-(2-cyanopyrrol-1-yl)-2-ethoxy)-6-(3-(1-piperazin-1-yl) propoxy) quinoline-4-carboxamide (45 mg, 0.1 mmol) were added to the mixed solution in sequence. After reacting overnight at room temperature, 30 mL of ethyl acetate was added to the mixed solution, and washed with water (10 mL×2) and brine (10 mL). The organic phase was dried over anhydrous magnesium sulfate and filtered to remove solid impurities. The organic phase in the filtrate was removed under reduced pressure by using a rotary evaporator and separated through a silica gel column with dichloromethane/ethanol/ammonia (v/v/v, 90/10/1), and then the components were collected. The solvent was removed under reduced pressure to give 45 mg of pale yellow oil.

The resulting yellowish oil was dissolved in 5 mL of trifluoroacetic acid and stirred at room temperature for 3 hours. The solvent was removed under reduced pressure by using a rotary evaporator, and the residue was separated by a semi-preparative high-performance liquid chromatography column (HPLC) to give 15.2 mg of product A1 (10.5% yield). A1 was the target product based on analyses by LC-MS. HRMS (ESI) theoretical molecular weight $C_{50}H_{61}N_8O_{12}$ $(M+H)^+$ was 964.4331, and the measured molecular weight was 964.4376. In above mentioned semi-preparative high-performance liquid chromatography column (HPLC), the first mobile phase was 0.1% aqueous solution of trifluoroacetic acid, the second mobile phase was acetonitrile. The gradient elution conditions were as follows: 0 min, 100% of the first mobile phase; 0-10 min, 100%-0% of the first mobile phase; the flow rate of the mobile phase was 4 ml/min.

Example 2

Synthesis of radioactively labeled ligand A2 for fibroblast activation protein-alpha (FAP) imaging agent.

2,2'-(ethane-1,2-diylbis((5-(3-(4-((2-((S)-2-cyanopyrrolidin-1-yl)-2-oxyethyl)carbamoyl)quinolin-6-yl)oxy)propyl)piperazin-1-yl)-3-oxypropyl)-2-hydroxybenzyl)azacyclic Diacetic Acid Synthesis reaction equation:

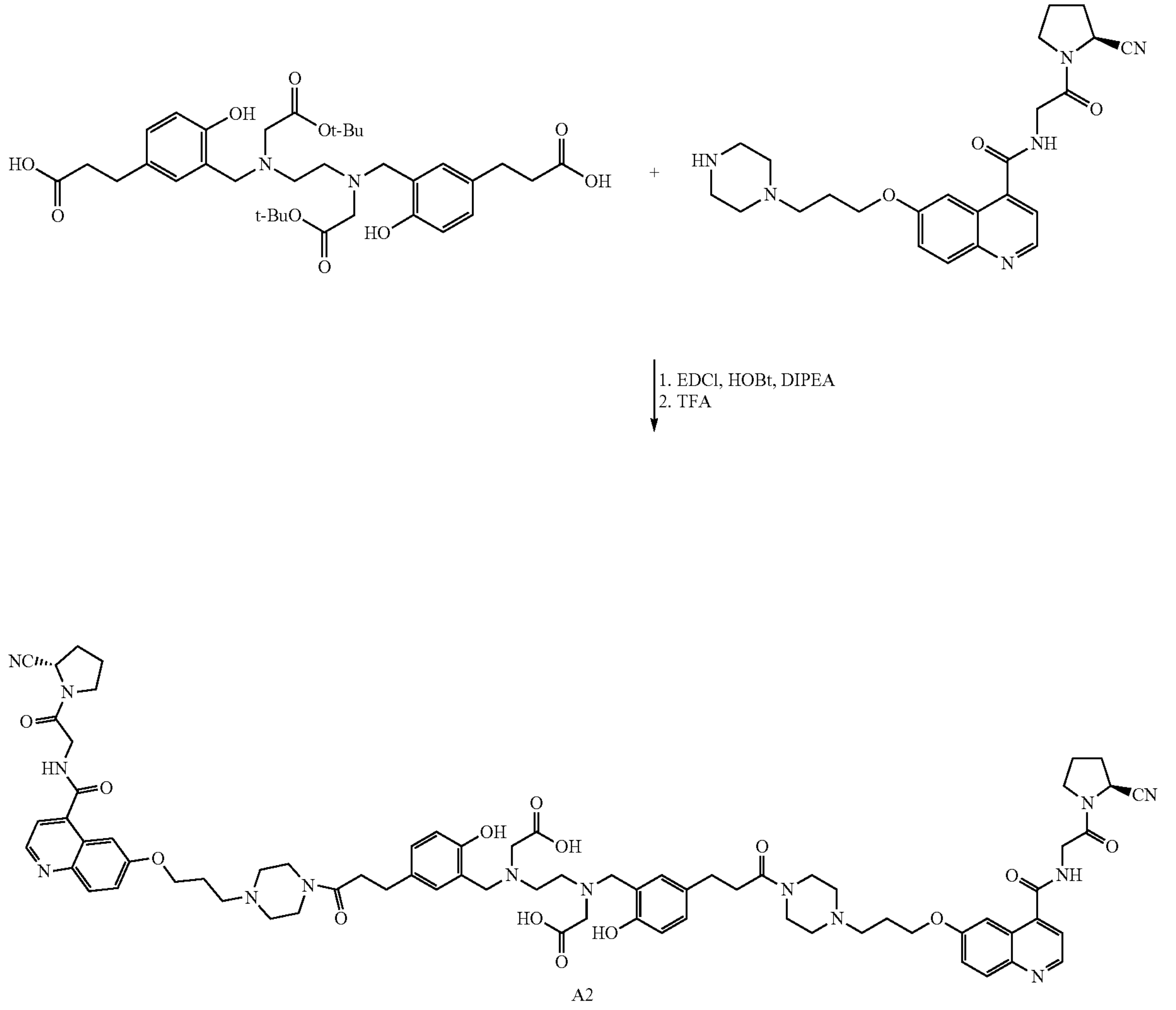

A2

Synthetic Methods

Compound 3,3'-(((2,2,13,13-tetramethyl-4,11-dioxo-3,12-dioxa-6,9-diaztetradecane-6,9-diyl) bis (methylene)) bis (4-hydroxy-3,1-phenylene) dipropanoic acid (128 mg, 0.2 mmol) was dissolved in 5 mL of anhydrous dimethylformamide, 1-(3-dimethylaminopropyl)-3-ethylcarbodiimide (EDCI, 57 mg, 0.3 mmol), 1-hydroxybenzotriazole (HOBt, 51.3 mg, 0.3 mmol), N,N-diisopropylethylamine (DIPEA, 82.6 mg, 0.64 mmol) and (S)—N-(2-(2-cyanopyrrol-1-yl)-2-ethoxy)-6-(3-(1-piperazin-1-yl) propoxy) quinoline-4-carboxamide (45 mg, 0.1 mmol) were added to the above mixture in sequence. After reacting overnight at room temperature, 30 mL of ethyl acetate was added to the mixture solution, washed with water (10 mL×2) and brine (10 mL). The organic phase was dried over anhydrous magnesium sulfate and filtered to remove solid impurities. The organic phase in the filtrate was removed under reduced pressure by using a rotary evaporator and separated through a silica gel column with dichloromethane/ethanol/ammonia (v/v/v, 90/10/1), and then the components were collected. The solvent was removed under reduced pressure to give 80 mg of pale yellow oil.

The resulting yellowish oil was dissolved in 10 mL of trifluoroacetic acid and stirred at room temperature for 3 hours. The solvent was removed under reduced pressure by using a rotary evaporator, and the residue was separated by a semi-preparative high-performance liquid chromatography column (HPLC) to give 25.9 mg of product A2 (41% yield). A2 was the target product based on analyses by LC-MS. HRMS (ESI) theoretical molecular weight $C_{74}H_{89}N_{14}O_{14}$ $(M+H)^+$ was 1397.6683, and the measured molecular weight was 1397.6746. In above mentioned semi-preparative high-performance liquid chromatography column (HPLC), the first mobile phase was 0.1% aqueous solution of trifluoro-acetic acid, the second mobile phase was acetonitrile. The gradient elution conditions were as follows: 0 min, 100% of the first mobile phase; 0-10 min, 100%-0% of the first mobile phase; the flow rate of the mobile phase was 4 ml/min.

Example 3

$^{68}$Ga Radioactively Labeling of Radioactively Labeled Ligand A1

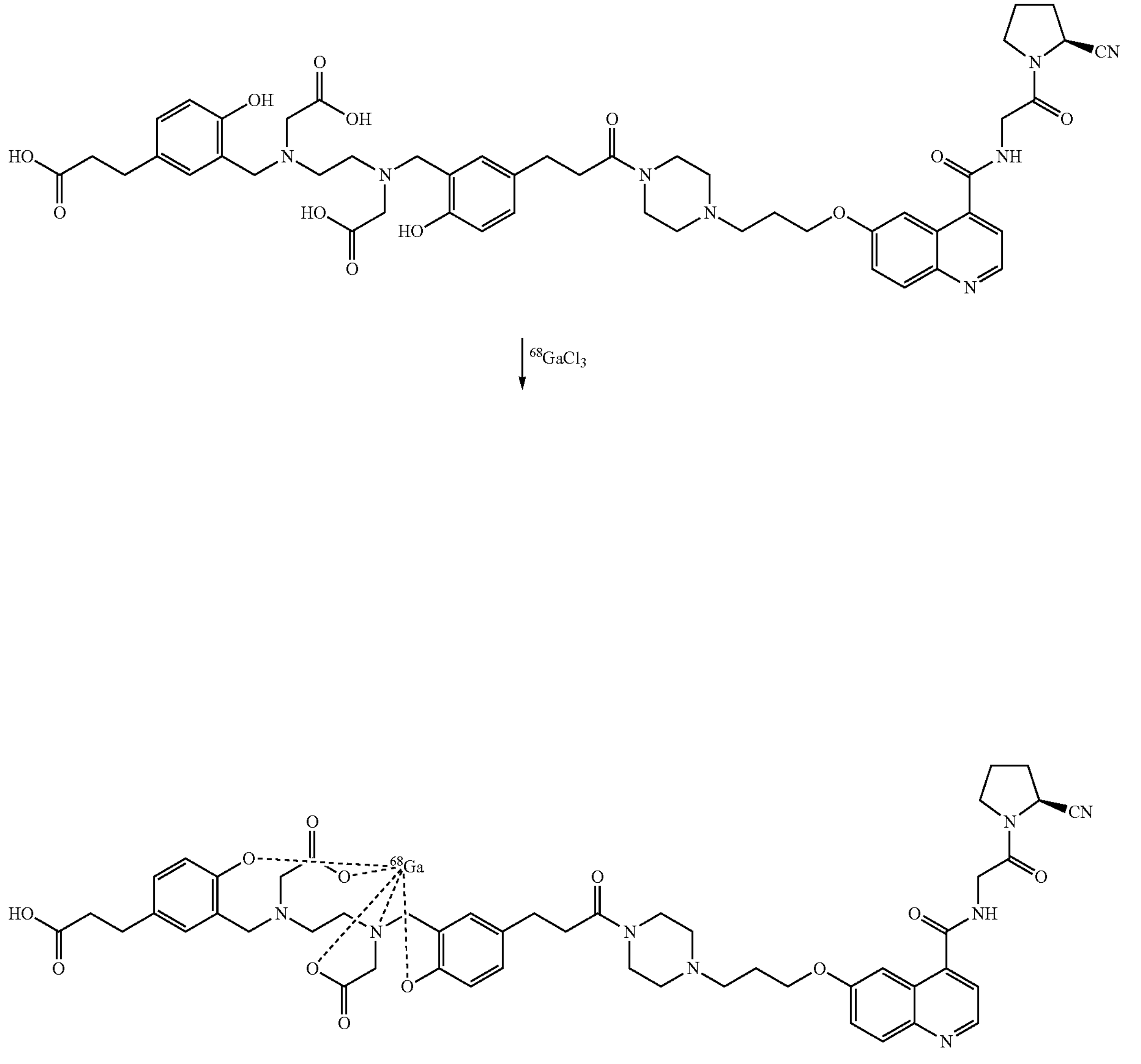

(1) 1 mg of compound A1 ((S)-3-(3-((carboxymethyl) (2-((carboxymethyl) (5-(3-(4-((4-((2-(2-cyanopyrrolidin-1-yl)-2-oxyethyl) carbamoyl) quinolin-6-yl) oxy) propyl) piperazin-1-yl)-3-oxypropyl)-2-hydroxybenzyl) amino) ethyl) amino) methyl)-4-hydroxyphenyl) propanoic acid) was dissolved in 1 mL of 0.05N sodium acetate buffer, and sodium hydroxide solution was added to adjust the pH value to 5, then a solution of compound A1 at a concentration of 1 mg/mL was obtained.

(2) The germanium gallium generator was rinsed with 4 mL of high-purity 0.05N hydrochloric acid solution, and a $^{68}GaCl_3$ hydrochloric acid solution with an activity of 8-10 mCi was obtained.

(3) 50 μL of a sodium acetate buffer at a concentration of 0.5M was added in a reaction vessel, then 30 μL of the compound A1 solution prepared in step-1 was added and mixed evenly, and then 500 μL of $^{68}GaCl_3$ hydrochloric acid solution prepared in step-2 was added. The mixture was shaken evenly and reacted at room temperature for 10 to 30 min. After cooling to ambient temperature, the labeling yield was measured by a semi-preparative high-performance liquid chromatography column (HPLC), and the $^{68}$GaA1 was obtained.

In step-3 mentioned semi-preparative high-performance liquid chromatography column (HPLC), the first mobile phase was 0.1% aqueous solution of trifluoroacetic acid, the second mobile phase was acetonitrile. The gradient elution conditions were as follows: 0 min, 100% of the first mobile phase; 0-10 min, 100%-0% of the first mobile phase; the flow rate of the mobile phase was 1 ml/min.

The HPLC chromatogram of $^{68}$GaA1-labeled reaction solution prepared in step-3 of Example 3 of the present invention was shown in FIG. 1.

Example 4

$^{68}$Ga Radioactively Labeling of Radioactively Labeled Ligand A2

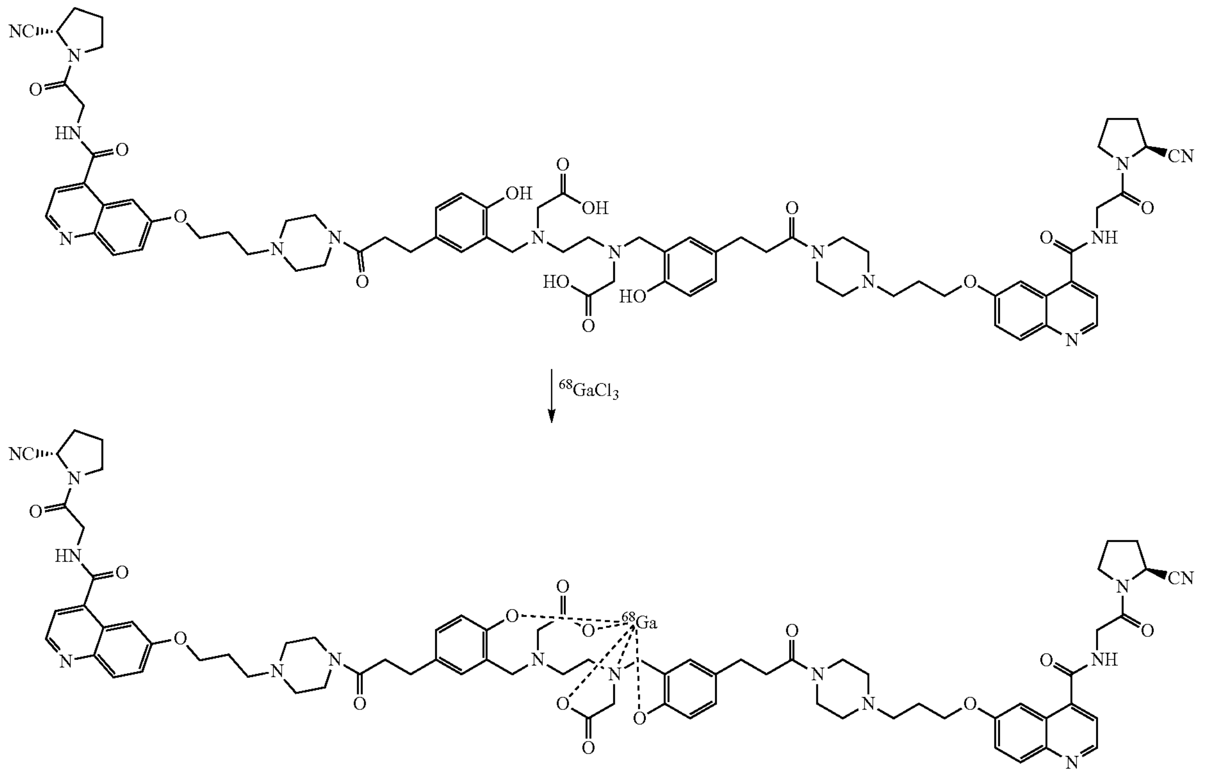

(1) 1 mg of compound A2 (2,2'-(ethane-1,2-diylbis ((5-(3-(4-((2-((S)-2-cyanopyrrolidin-1-yl)-2-oxyethyl) carbamoyl) quinolin-6-yl) oxy) propyl) piperazin-1-yl)-3-oxypropyl)-2-hydroxybenzyl) azacyclic diacetic acid) was dissolved in 1 mL of 0.05N sodium acetate buffer, and sodium hydroxide solution was added to adjust the pH value to 5, then a solution of compound A2 at a concentration of 1 mg/mL was obtained.

(2) The germanium gallium generator was rinsed with 4 mL of high-purity 0.05N hydrochloric acid solution, and a $^{68}GaCl_3$ hydrochloric acid solution with an activity of 8-10 mCi was obtained.

(3) 50 μL of a sodium acetate buffer at a concentration of 0.5M was added in a reaction vessel, then 30 μL of the compound A2 solution prepared in step-1 was added and mixed evenly, and then 500 μL of $^{68}GaCl_3$ hydrochloric acid solution prepared in step-2 was added. The mixture was shaken evenly and reacted at room temperature for 10 to 30 min. After cooling to ambient temperature, the labeling yield was measured by a semi-preparative high-performance liquid chromatography column (HPLC), and the $^{68}$GaA2 was obtained.

In step-3 mentioned semi-preparative high-performance liquid chromatography column (HPLC), the first mobile phase was 0.1% aqueous solution of trifluoroacetic acid, the second mobile phase was acetonitrile. The gradient elution conditions were as follows: 0 min, 100% of the first mobile phase; 0-10 min, 100%-0% of the first mobile phase; the flow rate of the mobile phase was 1 ml/min.

Figure 2:
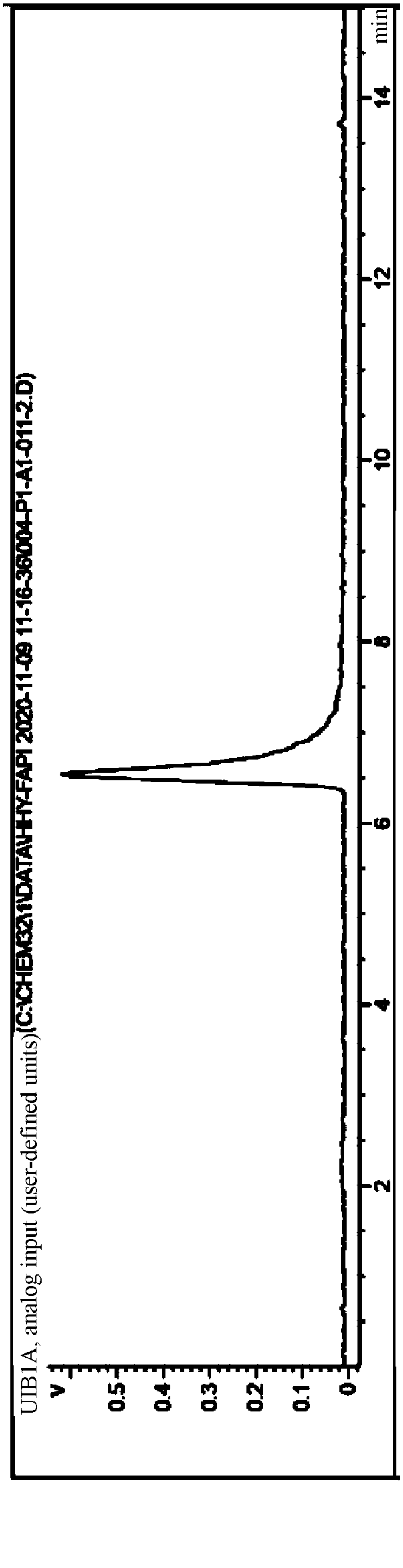
FIG. 2. HPLC chromatogram of $^{68}$GaA2-labeled reaction solution prepared in step-3 of Example 4 of the present invention.

The HPLC chromatogram of $^{68}$GaA2-labeled reaction solution prepared in step-3 of Example 4 of the present invention was shown in FIG. 2.

The radioactively labeled ligand for fibroblast activation protein-alpha (FAP) imaging agent of this present invention has a good $^{68}$Ga labeling property, rapid and efficient in preparation, the resulting agent has high stability. The $^{68}$Ga molecular probe contains (S)—N-(2-(2-cyanopyrrol-1-yl)-2-ethoxy)-6-(3-(-1-piperazin-1-yl) propoxy) quinoline-4-carboxamide group, which has good FAP affinity.

It is expected that $^{68}$GaA1 and $^{68}$GaA2 have a good affinity for FAP tumors. Therefore, the molecular probe made of radioactively labeled ligand of $^{68}$Ga-labeled fibroblast activation protein-alpha (FAP) targeted molecular probe of the present invention may serve as a tumor positron molecular probe.

It is to be understood that the described examples herein are only some preferred examples of the present invention, there is no intent to limit the scope of implementation of the present invention. Equivalent changes and modifications made according to the patent scope and specification of the present invention should still fall within the scope of the present invention.

The invention claimed is:

1. A radioactively labeled ligand for fibroblast activation protein-alpha (FAP) imaging agent, having a structural formula of

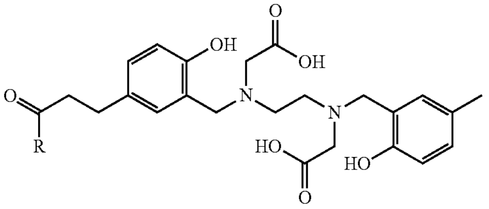

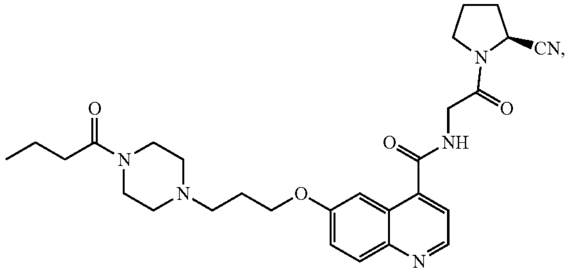

wherein R is —OH or

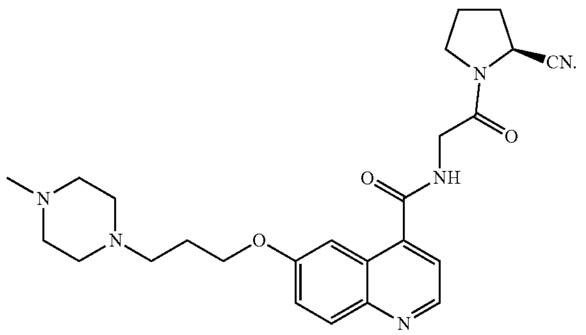 [SMILES: CN1CCN(CCCOc2ccc3nccc(C(=O)NCC(=O)N4CCC[C@H]4C#N)c3c2)CC1]

2. A radioactively labeled fibroblast activation protein-alpha (FAP) imaging agent, having a structural formula of $^{68}$GaA1 or $^{68}$GaA2:

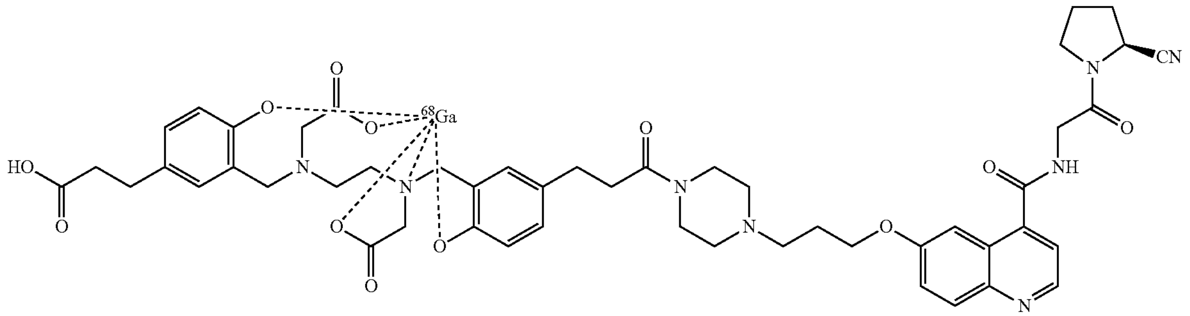

$^{68}$GaA1

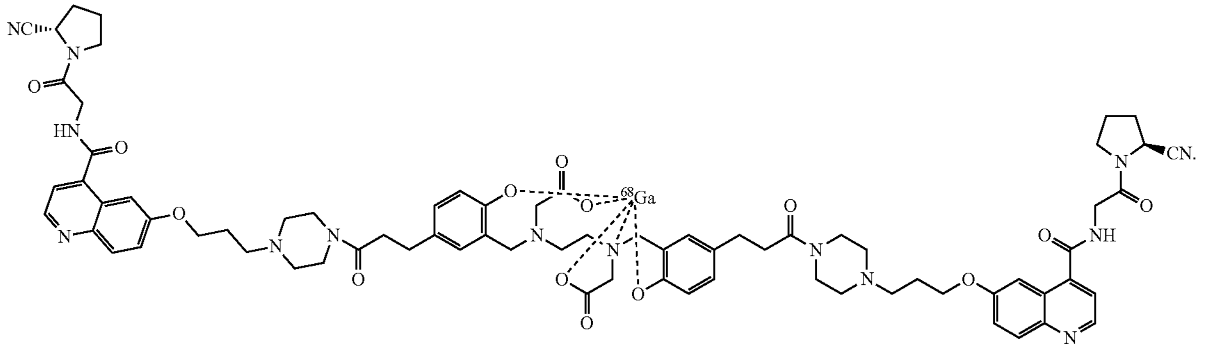

$^{68}$GaA2

3. A $^{68}$Ga-labeled positron drug, comprising the radioactively labeled fibroblast activation protein-alpha (FAP) imaging agent according to claim 2.

4. A method for diagnosing tumors, comprising administering to a subject in need of the $^{68}$Ga-labeled positron drug according to claim 3.

5. A preparation method of the radioactively labeled ligand according to claim 1, comprising the following steps:

subjecting a bifunctional linker HBED-CC and a FAP inhibitor to a condensation reaction in the presence of a base and a condensing agent to obtain a condensation product; removing a protecting group with an acid from the condensation product to give the fibroblast activation protein (FAP) targeted imaging agent, wherein the bifunctional linker HBED-CC and the FAP inhibitor have the following structural formulae:

HBED-CC

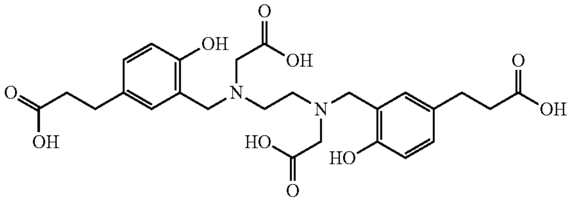

FAPi

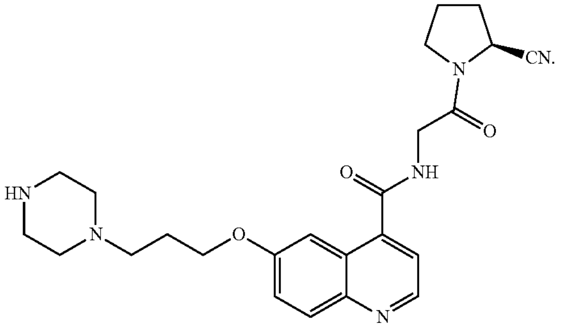

6. A preparation method of the radioactively labeled ligand according to claim 1, wherein the radioactively labeled ligand for fibroblast activation protein-alpha (FAP) imaging agent is(S)-3-(3-((carboxymethyl) (2-((carboxymethyl) (5-(3-(4-((4-((2-(2-cyanopyrrolidin-1-yl)-2-oxyethyl) carbamoyl) quinolin-6-yl) oxy) propyl) piperazin-1-yl)-3-oxypropyl)-2-hydroxybenzyl) amino) ethyl) amino) methyl)-4-hydroxyphenyl) propanoic acid, the preparation method comprising the following steps:

dissolving a compound 3, 3'-(((2, 2, 13, 13-tetramethyl-4, 11-dioxo-3, 12-dioxa-6, 9-diazatetradecane-6, 9-diyl) bis(methylene)) bis(4-hydroxy-3, 1-phenylene) dipropanoic acid in anhydrous dimethylformamide, adding 1-(3-dimethylaminopropyl)-3-ethylcarbodiimide, 1-hydroxybenzotriazole, N, N-diisopropylethylamine and(S)—N-(2-(2-cyanopyrrol-1-yl)-2-ethoxy)-6-(3-(1-piperazin-1-yl) propoxy) quinoline-4-carboxamide to the mixed solution in sequence;

after reacting overnight at room temperature, adding ethyl acetate to the mixed solution, and washing with water and brine;

drying the organic phase over anhydrous magnesium sulfate and filtering to remove solid impurities; and removing the organic phase in the filtrate under reduced pressure by using a rotary evaporator, separating through a silica gel column with dichloromethane/ethanol/ammonia, collecting the components and removing the solvent under reduced pressure to give (S)-3-(3-((carboxymethyl) (2-((carboxymethyl) (5-(3-(4-((4-((2-(2-cyanopyrrolidin-1-yl)-2-oxyethyl) carbamoyl) quinolin-6-yl) oxy) propyl) piperazin-1-yl)-3-oxypropyl)-2-hydroxybenzyl) amino) ethyl) amino) methyl)-4-hydroxyphenyl) propanoic acid as a pale yellow oil.

7. A preparation method of the radioactively labeled ligand according to claim 1, wherein the radioactively labeled ligand for fibroblast activation protein-alpha (FAP) imaging agent is 2, 2'-(ethane-1, 2-diylbis ((5-(3-(4-((2-((S)-2-cyanopyrrolidin-1-yl)-2-oxyethyl) carbamoyl) quinolin-6-yl) oxy) propyl) piperazin-1-yl)-3-oxypropyl)-2-hydroxybenzyl) azacyclic diacetic acid, the preparation method comprising the following steps:

dissolving a compound 3, 3'-(((2, 2, 13, 13-tetramethyl-4, 11-dioxo-3, 12-dioxa-6, 9-diazatetradecane-6, 9-diyl) bis(methylene)) bis(4-hydroxy-3, 1-phenylene) dipropanoic acid in anhydrous dimethylformamide, adding 1-(3-dimethylaminopropyl)-3-ethylcarbodiimide, 1-hydroxybenzotriazole, N, N-diisopropylethylamine and(S)—N-(2-(2-cyanopyrrol-1-yl)-2-ethoxy)-6-(3-(1-piperazin-1-yl) propoxy) quinoline-4-carboxamide to the mixed solution in sequence;

after reacting overnight at room temperature, adding ethyl acetate to the mixed solution, and washing with water and brine;

drying the organic phase over anhydrous magnesium sulfate and filtering to remove solid impurities; and removing the organic phase in the filtrate under reduced pressure by using a rotary evaporator, separating through a silica gel column with dichloromethane/ethanol/ammonia, collecting the components and removing the solvent under reduced pressure to give 2, 2'-(ethane-1, 2-diylbis ((5-(3-(4-((2-((S)-2-cyanopyrrolidin-1-yl)-2-oxyethyl) carbamoyl) quinolin-6-yl) oxy) propyl) piperazin-1-yl)-3-oxypropyl)-2-hydroxybenzyl) azacyclic diacetic acid as a pale yellow oil.

* * * * *